(12) United States Patent
Saurat et al.

(10) Patent No.: US 11,690,886 B2
(45) Date of Patent: Jul. 4, 2023

(54) **COMBINATION OF A RETINOID AND AN EXTRACT OF *SILYBUM MARIANUM* (L.) GAERTN**

(71) Applicant: PIERRE FABRE DERMO-COSMETIQUE, Boulogne-Billancourt (FR)

(72) Inventors: Jean-Hilaire Saurat, Geneva (CH); Olivier Sorg, Geneva (CH)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 427 days.

(21) Appl. No.: 16/955,729

(22) PCT Filed: Dec. 20, 2018

(86) PCT No.: PCT/EP2018/086326
§ 371 (c)(1),
(2) Date: Jun. 18, 2020

(87) PCT Pub. No.: WO2019/122203
PCT Pub. Date: Jun. 27, 2019

(65) Prior Publication Data
US 2021/0069273 A1     Mar. 11, 2021

(30) Foreign Application Priority Data
Dec. 20, 2017  (FR) ...................................... 1762606

(51) Int. Cl.
| | | |
|---|---|---|
| *A61K 36/28* | (2006.01) | |
| *A61K 31/11* | (2006.01) | |
| *A61K 31/575* | (2006.01) | |
| *A61K 47/02* | (2006.01) | |
| *A61K 47/06* | (2006.01) | |
| *A61K 47/10* | (2017.01) | |
| *A61K 47/14* | (2017.01) | |
| *A61K 47/18* | (2017.01) | |
| *A61K 47/26* | (2006.01) | |
| *A61K 47/32* | (2006.01) | |
| *A61K 47/44* | (2017.01) | |
| *A61P 17/08* | (2006.01) | |
| *A61P 17/10* | (2006.01) | |
| *A61K 31/07* | (2006.01) | |

(52) U.S. Cl.
CPC .............. *A61K 36/28* (2013.01); *A61K 31/11* (2013.01); *A61K 31/575* (2013.01); *A61K 47/02* (2013.01); *A61K 47/06* (2013.01); *A61K 47/10* (2013.01); *A61K 47/14* (2013.01); *A61K 47/18* (2013.01); *A61K 47/183* (2013.01); *A61K 47/26* (2013.01); *A61K 47/32* (2013.01); *A61K 47/44* (2013.01); *A61P 17/08* (2018.01); *A61P 17/10* (2018.01); *A61K 2236/333* (2013.01)

(58) Field of Classification Search
CPC .......... A61K 2236/333; A61K 2300/00; A61K 31/07; A61K 31/11; A61K 31/203; A61K 31/575; A61K 36/28; A61K 47/02; A61K 47/06; A61K 47/10; A61K 47/14; A61K 47/18; A61K 47/183; A61K 47/26; A61K 47/32; A61K 47/44; A61P 17/08; A61P 17/10
See application file for complete search history.

(56) References Cited

U.S. PATENT DOCUMENTS

| | | | |
|---|---|---|---|
| 4,749,573 A | 6/1988 | Bonne et al. | |
| 8,679,552 B2 * | 3/2014 | Guthery ................. | A61P 17/10 424/725 |
| 2019/0054062 A1 | 2/2019 | Merary et al. | |

FOREIGN PATENT DOCUMENTS

| | | |
|---|---|---|
| CN | 1662216 A | 8/2005 |
| CN | 104673486 A | 6/2015 |
| GB | 2 084 569 A | 4/1982 |
| JP | 62-223106 A | 10/1987 |
| JP | 2000-169332 A | 6/2000 |
| KR | 10-2010-0079586 A | 7/2010 |
| WO | WO 01/64211 A1 | 9/2001 |
| WO | WO 02/02074 A2 | 1/2002 |
| WO | WO 2017/037534 A1 | 3/2017 |

OTHER PUBLICATIONS

Fathi-Achachlouei et al., "Milk Thistle Seed Oil Constituents from Different Varieties Grown in Iran," Journal of the American Oil Chemists' Society, vol. 86, Jul. 2003, pp. 643-649.
International Search Report dated Apr. 23, 2019, in PCT Application No. PCT/EP2018/086326 (four pages).
Abstract of Han, et al., "Composition useful as external skin composition and cosmetics composition for preventing atopic dermatitis and suppressing skin rash, comprises milk thistle extract," XP-002732291, WPI/Thomson (two pages).
Röllman, O. and Vahlquist, A. "Vitamin A in skin and serum—studies of acne vulgaris, atopic dermatitis, ichthyosis vulgaris and lichen planus." *Br. J. Dermatol.* 113, 405-413 (1985).
Everts, H. B., "Endogenous retinoids in the hair follicle and sebaceous gland" *Biochim. Biophys. Acta* 1821(1), 222-229 (2012).
Sorg, O. and Saurat, J. H. "Topical retinoids in skin ageing: A focused update with reference to sun induced epidermal vitamin A deficiency." *Dermatology* 228(4), 314-325 (2014).

(Continued)

Primary Examiner — Jeffrey T. Palenik
(74) Attorney, Agent, or Firm — Birch, Stewart, Kolasch & Birch, LLP

(57) ABSTRACT

The present invention relates to the combination of a retinoid and an extract of *Silybum marianum* (L.) Gaertn., the dermatological and dermocosmetic compositions containing such a combination, as well as their uses as a medicinal product, in particular in the treatment of acne, seborrhea, seborrhoeic dermatitis and/or rosacea.

17 Claims, 5 Drawing Sheets

(56) References Cited

OTHER PUBLICATIONS

Kuki, A., et al., "Identification of Silymarin Constituents," *Chromatographia* vol. 75, pp. 175-180 (2012).
Parry, Jr., John Wynne, Thesis of 2006, "Value-adding factors in cold pressed edible seed oils and flours" Abstract, pp. i-viii and 1-143.
Thiboutot et al., "Acne Vulgaris and the Epidermal Barrier" The Journal of Clinical and Aesthetic Dermatology (2013), vol. 6, No. 1, pp. 18-24.

* cited by examiner

COMBINATION OF A RETINOID AND AN EXTRACT OF *SILYBUM MARIANUM* (L.) GAERTN

This application is a United States national stage entry under 35 U.S.C. § 371 of International Application No. PCT/EP2018/086326, filed on Dec. 20, 2018, which claims priority to French Patent Application No. 1762606, filed on Dec. 20, 2017. The contents of these applications are each incorporated herein by reference in their entirety.

TECHNICAL FIELD

The present invention relates to a combination of a retinoid and an extract of *Silybum marianum* (L.) Gaertn., as well as a dermatological or dermocosmetic composition, preferably topical, containing such a combination, in particular for the treatment of acne, seborrhea, rosacea and/or seborrhoeic dermatitis.

PRIOR ART

The scientific name *Silybum marianum* (L.) Gaertn. refers to a plant belonging to the family Asteraceae, annual or biennial with a sturdy stem that can reach more than one meter in height. Its large, glossy, alternate, stipulate-free leaves are mottled white and edged with hard, pointed spines. The flowers are grouped in terminal flower heads, often solitary. They are surrounded by large spiny bracts with very sharp tips. The 5-lobed, tubular flowers are purplish-purple in color. Fruits are glossy, black or yellow-marbled achenes, topped by a ring of toothed bristles at the base. The vernacular name of this plant is milk thistle.

The achene (often erroneously referred to as the seed in the literature) of *Silybum marianum* (L.) Gaertn. and its preparations are traditionally used orally, in the symptomatic treatment of digestive functional disorders attributed to a hepatic origin.

In the literature, the main active ingredient of the achene of *Silybum marianum* (L.) Gaertn. is silymarin, a mixture of several flavonolignans (mainly silybin, isosilybin, silychristin and silydianin). Achenes contain up to 3% by weight of silymarin. They also contain oil (20-30% by weight), mucilages and proteins.

In addition, vitamin A deficiency has been shown in the skin of acne patients (Millman, O., and Vahlquist, A. (1985). Vitamin A in skin and serum—studies of acne vulgaris, atopic dermatitis, ichthyosis vulgaris and lichen planus. Br. J. Dermatol. 113(4), 405-413) and a deficiency in its metabolism has been described in pilosebaceous epithelium (Everts, H. B. (2012). Endogenous retinoids in the hair follicle and sebaceous gland. Biochim Biophys. Acta 1821(1), 222-229). Retinaldehyde in topical application allows the delivery of the different components of Vitamin A in human skin (Sorg, O., and Saurat, J. H. (2014). Topical retinoids in skin ageing: A focused update with reference to sun induced epidermal vitamin A deficiency. Dermatology 228(4), 314-325), a property that is already used in the prevention and treatment of acne-prone skin.

SUMMARY OF THE INVENTION

In this context, the Applicant surprisingly demonstrated that a retinoid, such as retinaldehyde (also called retinal), in combination with an extract of *Silybum marianum*, presented improved properties for the treatment of acne, seborrhea, rosacea or seborrheic dermatitis. In particular, the results of studies obtained demonstrated the synergistic role of retinaldehyde associated with an extract of *Silybum marianum* in the production of retinoid acids by skin cells.

A subject matter of the invention therefore relates to a combination comprising a retinoid and an extract of *Silybum marianum* (L.) Gaertn.

A further subject matter of the invention relates to a combination comprising a retinoid and an extract of *Silybum marianum* (L.) Gaertn. for use as a medicinal product.

A further subject matter of the invention relates to a combination comprising a retinoid and an extract of *Silybum marianum* (L.) Gaertn. for use in the treatment of acne, seborrhea, rosacea and/or seborrhoeic dermatitis.

A further subject matter of the invention relates to the use of a combination comprising a retinoid and an extract of *Silybum marianum* (L.) Gaertn. for the manufacture of a medicinal product for the treatment of acne, seborrhea, rosacea and/or seborrhoeic dermatitis.

A further subject matter of the invention relates to the use of a combination comprising a retinoid and an extract of *Silybum marianum* (L.) Gaertn. in the treatment of acne, seborrhea, rosacea and/or seborrhoeic dermatitis.

A further subject matter of the invention relates to a method for treating acne, seborrhea, rosacea and/or seborrheic dermatitis comprising administering to a person in need thereof an effective amount of a combination comprising a retinoid and an extract of *Silybum marianum* (L.) Gaertn.

A further subject matter of the invention relates to a dermatological or dermocosmetic composition, preferably topical, comprising a retinoid and an extract of *Silybum marianum* (L.) Gaertn. in combination with at least one dermatologically or dermocosmetically acceptable excipient.

A further subject matter of the invention relates to a dermatological or dermocosmetic composition, preferably topical, comprising a retinoid and an extract of *Silybum marianum* (L.) Gaertn. in combination with at least one dermatologically or dermocosmetically acceptable excipient for use in the treatment of acne, seborrhea, rosacea and/or seborrhoeic dermatitis.

A further subject matter of the invention relates to the use of a dermatological or dermocosmetic composition, preferably topical, comprising a retinoid and an extract of *Silybum marianum* (L.) Gaertn. in combination with at least one dermatologically or dermocosmetically acceptable excipient in the treatment of acne, seborrhea, rosacea and/or seborrhoeic dermatitis.

A further subject matter of the invention relates to a method for treating acne, seborrhea, rosacea and/or seborrhoeic dermatitis comprising administering, preferably topically, to a person in need thereof an effective amount of a dermatological or dermocosmetic composition comprising a retinoid and an extract of *Silybum marianum* (L.) Gaertn. in combination with at least one dermatologically or dermocosmetically acceptable excipient.

A further subject matter of the invention relates to a dermatological or dermocosmetic composition, preferably topical, comprising:
(i) a retinoid, and
(ii) an extract of *Silybum marianum* (L.) Gaertn.
as combination products, for simultaneous, separate or sequential use.

A further subject matter of the invention relates to a dermatological or dermocosmetic composition, preferably topical, comprising:

(i) a retinoid, and
(ii) an extract of *Silybum marianum* (L.) Gaertn.
as combination products, for simultaneous, separate or sequential use in the treatment of acne, seborrhea, rosacea and/or seborrheic dermatitis.

A further subject matter of the invention relates to the simultaneous, separate or sequential use of a retinoid and an extract of *Silybum marianum* (L.) Gaertn. in the treatment of acne, seborrhea, rosacea and/or seborrhoeic dermatitis.

A further subject matter of the invention relates to a method for treating acne, seborrhea, rosacea and/or seborrheic dermatitis comprising administering simultaneously, separately or sequentially an effective amount of a retinoid and an effective amount of an extract of *Silybum marianum* (L.) Gaertn. to a person in need thereof.

DETAILED DESCRIPTION

Definitions

In the present description, the plant *Silybum marianum* (L.) Gaertn. may be abbreviated as *Silybum marianum* and retinaldehyde may be abbreviated as RAL.

For the purposes of the present invention, "fatty acid" means a carboxylic acid $R1CO_2H$ whose chain R1 is a linear or branched hydrocarbon chain, saturated or comprising C=C double bonds, the carboxylic acid comprising from 16 to 22 carbon atoms (including the carbon atom of the carboxylic acid function).

For the purposes of the present invention, "free" fatty acid (including linoleic acid) means a fatty acid not bound to other molecules (e.g. to glycerol or derivatives thereof to give glycerides or to an alcohol to give a fatty ester).

For the purposes of the present invention, "$C_1$ to $C_3$ alcohol" means an alcohol R2OH whose chain R2 is a saturated, linear or branched hydrocarbon chain comprising 1 to 3 carbon atoms. It may be methanol, ethanol, n-propanol or isopropanol, in particular methanol, ethanol or isopropanol. Preferably it will be isopropanol.

"Dermatologically or dermocosmetically acceptable" means, in the present invention, that which is useful in the preparation of a dermatological or dermocosmetic composition which is generally safe, non-toxic and neither biologically nor otherwise undesirable and which is acceptable for therapeutic or cosmetic use, in particular by topical application.

In the present description, "about" means that the value concerned may be 10%, in particular 5%, or 1%, lower or higher than the value indicated.

For the purposes of the present invention, "dry extract" means an extract which is free of extraction solvent or which contains only insignificant trace amounts of extraction solvent. Such a dry extract thus contains only material derived from *Silybum marianum* (L.) Gaertn. It may also contain insignificant traces of extraction solvent.

For the purposes of the present invention, "isosilybin" means the two diastereoisomers isosilybin A and isosilybin B.

The term "silybin", also called "silibinin" in the art, means, within the meaning of the present invention, the four diastereoisomers silybin A, silybin B, 2,3-cis-silybin A and 2,3-cis-silybin B.

For the purposes of the present invention, "silychristin" means the two diastereoisomers silychristin A and silychristin B.

For the purposes of the present invention, "silymarin" means a purified extract of achenes of *Silybum marianum* (L.) Gaertn. comprising mainly (at least 95% by weight) a mixture of the following four flavonolignans: silybin, isosilybin, silychristin and silydianin (Kuki et al. 2012). A silymarin content of less than 0.2% by weight therefore means that the total amount of silymarin constituents is less than 0.2% by weight. Such a content can be determined in particular by high-performance liquid chromatography (HPLC) or ultra-high-performance liquid chromatography (UPLC) by calculating the total area of the peaks corresponding to all silymarin constituents, in particular by using a reference silymarin sample, which can be obtained for example from Sigma Aldrich, to determine the position of these peaks.

For the purposes of the present invention, "organic solvent immiscible with oil derived from achenes of *Silybum marianum* (L.) Gaertn." means an organic solvent which is not capable of mixing, or only partially mixing, with the oil obtained from the achenes of *Silybum marianum* (L.) Gaertn. so that the mixture of the organic solvent and the oil derived from achenes of *Silybum marianum* (L.) Gaertn. gives a heterogeneous mixture in which at least two distinct phases can be observed.

For the purposes of the present invention, "sterol" means a molecule having a sterane core whose carbon 3 carries a hydroxyl group OH, the sterane core having the following structure:

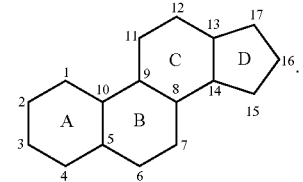

For the purposes of the present invention, "tocopherol" means α-tocopherol, β-tocopherol, γ-tocopherol and δ-tocopherol.

Retinoid

The retinoid used in the context of the present invention may be selected from retinol, retinaldehyde and retinoic acid in its various isomeric forms (in particular all-trans, 13-cis and 9-cis). Advantageously, the retinoid will be retinol or retinaldehyde. Preferably, the retinoid is retinaldehyde.

Extract of *Silybum marianum* (L.) Gaertn.

The extract used in the context of the present invention is an extract of *Silybum marianum*, and in particular an achene extract of *Silybum marianum*.

According to a particular embodiment, the extract according to the invention contains less than 0.2%, preferably less than 0.1% by weight of silymarin based on the weight of the dry extract.

According to a particular embodiment, the extract according to the invention contains at least 0.5% by weight, preferably at least 1.0% by weight of beta-sitosterol based on the weight of the dry extract. In particular, the extract according to the invention contains between 0.5% by weight and 2.5% by weight, in particular between 1.0% by weight and 2.0% by weight, for example about 1.5% by weight of beta-sitosterol based on the weight of the dry extract. Advantageously, the extract according to the invention contains less than 0.2%, preferably less than 0.1% by weight of silymarin based on the weight of the dry extract. The silymarin/beta-sitosterol weight ratio of the extract according to the invention may be less than 0.4, in particular less than 0.07. The extract according to the invention may also comprise between 2 and 7% by weight, in particular between 3 and 6% by weight, for example between 3 and 5% by weight of sterols based on the weight of the dry extract.

According to another particular embodiment, the extract according to the invention contains at least 3% by weight, preferably at least 4% by weight of free linoleic acid based on the weight of the dry extract. In particular, the extract according to the invention contains between 3% and 15% by weight, in particular between 4% and 10% by weight, in particular between 4% and 6% by weight, for example about 5% by weight of free linoleic acid based on the weight of the dry extract. Advantageously, the extract according to the invention contains less than 0.2%, preferably less than 0.1% by weight of silymarin based on the weight of the dry extract. The extract according to the invention may also comprise between 10% and 70%, in particular between 10% and 30% by weight, in particular between 15% and 25% by weight of free fatty acids based on the weight of the dry extract.

According to another particular embodiment, the extract according to the invention contains between 0.5% and 2.5% by weight, in particular between 1.0% and 2.0% by weight, for example about 1.5% by weight of beta-sitosterol based on the weight of the dry extract, and between 3% and 15% by weight, in particular between 4% and 10% by weight, in particular between 4% and 6% by weight, for example about 5% by weight of free linoleic acid based on the weight of the dry extract. Advantageously, the extract according to the invention contains less than 0.2%, preferably less than 0.1% by weight of silymarin based on the weight of the dry extract. The silymarin/beta-sitosterol weight ratio of the extract according to the invention may be less than 0.4, in particular less than 0.07. The extract according to the invention may also comprise between 2 and 7% by weight, in particular between 3 and 6% by weight, for example between 3 and 5% by weight of sterols based on the weight of the dry extract and between 10% and 50%, in particular between 10% and 30% by weight, in particular between 15% and 25% by weight of free fatty acids based on the weight of the dry extract.

The extract according to the invention contains at least 0.01% by weight, in particular at least 0.05% by weight of tocopherols, based on the weight of the dry extract. In particular, the extract according to the invention contains between 0.01% by weight and 0.5% by weight, in particular between 0.05% by weight and 0.2% by weight, for example about 0.1% by weight of tocopherols based on the weight of the dry extract. Advantageously, the extract according to the invention contains less than 0.2%, preferably less than 0.1% by weight of silymarin based on the weight of the dry extract. The silymarin/tocopherols weight ratio of the extract according to the invention may be less than 1, in particular less than 0.1.

According to another particular embodiment, the extract according to the invention contains less than 0.2%, preferably less than 0.1% by weight of silymarin based on the weight of the dry extract; between 0.5% and 2.5% by weight, in particular between 1.0% and 2.0% by weight, for example about 1.5% by weight of beta-sitosterol based on the weight of the dry extract; between 3% and 15% by weight, in particular between 4% and 10% by weight, in particular between 4% and 6% by weight, for example about 5% by weight of free linoleic acid based on the weight of the dry extract; and between 0.01% and 0.5% by weight, in particular between 0.05% and 0.2% by weight, for example about 0.1% by weight of tocopherols based on the weight of the dry extract. The extract according to the invention may also comprise between 2 and 7% by weight, in particular between 3 and 6% by weight, for example between 3 and 5% by weight of sterols based on the weight of the dry extract and between 10% and 50%, in particular between 10% and 30% by weight, in particular between 15% and 25% by weight of free fatty acids based on the weight of the dry extract. The silymarin/beta-sitosterol weight ratio of the extract according to the invention may be in particular less than 0.4, in particular less than 0.07. The silymarin/tocopherols weight ratio of the extract according to the invention may be in particular less than 1, in particular less than 0.1.

Preferably, the extract according to the present invention will be a dry extract.

The extract according to the present invention may be obtained by extraction of an oil derived from achenes of *Silybum marianum* (L.) Gaertn. by an extraction solvent comprising, in particular consisting of, an aqueous hydrotropic solution, subcritical water or an organic solvent immiscible with the oil derived from achenes of *Silybum marianum* (L.) Gaertn. optionally in admixture with water; in particular an organic solvent immiscible with the oil derived from achenes of *Silybum marianum* (L.) Gaertn., such as a $C_1$ to $C_3$ alcohol, optionally in admixture with water.

In particular, the extraction solvent will comprise, in particular will consist of, methanol, ethanol or isopropanol, optionally in admixture with water, in particular in an organic solvent/water volume ratio between 80/20 and 100/0, in particular between 85/15 and 95/5, in particular of about 90/10. Advantageously, it will be in an isopropanol/water mixture, in particular in a volume ratio of about 90/10.

The oil from *Silybum marianum* achenes can be advantageously obtained by extraction from *Silybum marianum* (L.) Gaertn. achenes (the achenes may be whole or in pieces), in particular by pressing, advantageously by cold pressing (i.e. without heating, at room temperature).

The step of extraction of the oil from *Silybum marianum* achenes can be carried out by mixing the oil with the extraction solvent for 1 to 12 h and in particular at a temperature between 15 and 25° C., in particular about 20° C. The quantity of extraction solvent used to carry out this extraction will advantageously be from 0.5 to 3 g, in particular from 1 to 3 g for 1 g of oil.

The extraction phase thus obtained is then separated from the lipid phase, before being dried and evaporated, partially or totally, in particular under vacuum, in order to substantially eliminate the extraction solvent and obtain either the dry extract if the solvent is totally eliminated, or the concentrated extract which is diluted in residual solvent.

Combination According to Invention

The combination according to the invention comprises a retinoid as defined above and an extract of *Silybum marianum* (L.) Gaertn. as defined above.

The combination according to the invention will preferably be a combination of retinaldehyde as retinoid with an extract of *Silybum marianum*, in particular an achene extract of *Silybum marianum*, essentially free of silymarin, i.e. comprising less than 0.2%, preferably less than 0.1% by weight of silymarin based on the weight of the dry extract.

Dermatological and Dermocosmetic Compositions According to the Invention

The present invention also has as its subject matter a dermatological or dermocosmetic composition comprising at least one combination as defined above in combination with at least one dermatologically or dermocosmetically acceptable excipient, more particularly intended for topical application, in particular to the skin.

The dermatological and dermocosmetic compositions according to the invention may be presented in the forms which are usually known for topical administration, i.e. in particular lotions, foams, gels, dispersions, emulsions, sprays, serums, masks or creams, with excipients allowing in particular cutaneous penetration in order to improve the properties and accessibility of the active principle. Advantageously, it will be a cream.

These compositions generally contain, in addition to the ingredients of the combination according to the present invention, a physiologically acceptable medium, generally water- or solvent-based, for example alcohols, ethers or glycols. They may also contain surface-active agents, complexing agents, preservatives, stabilizing agents, emulsifiers, thickeners, gelling agents, humectants, emollients, trace elements, essential oils, perfumes, dyes, mattifying agents, chemical or mineral filters, moisturizing agents, thermal waters, etc.

These compositions may also contain other active ingredients leading to a complementary or possibly synergistic effect.

Advantageously, the compositions according to the present invention will comprise 0.01 to 10% by weight, preferably 0.05 to 5% by weight, of an extract of *Silybum marianum* according to the invention (preferably by weight of dry extract) with respect to the total weight of the composition.

Advantageously, the compositions according to the present invention will comprise 0.001 to 5% by weight, preferably 0.01 to 1% by weight, of the retinoid with respect to the total weight of the composition.

Therapeutic Applications

The combinations according to the invention and the dermatological or dermocosmetic compositions according to the invention are useful in the treatment of acne (for example juvenile acne, also called adolescent acne, or late acne, which may be cystic), seborrhea, seborrhoeic dermatitis and/or rosacea, preferably by topical application, in particular to the skin.

The present invention is illustrated by the following non-limiting examples.

FIGURES

EXAMPLES

Figure 1:
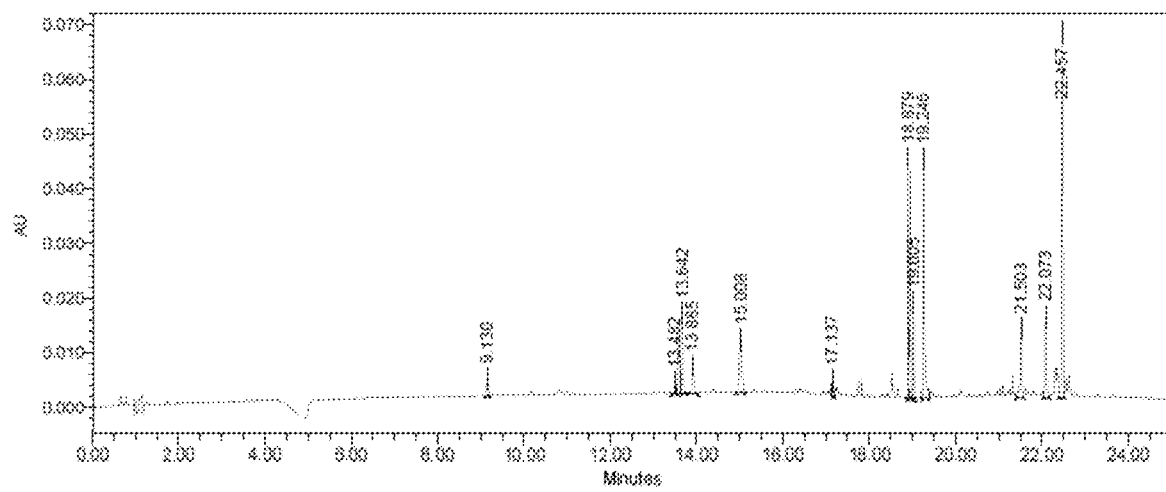
FIG. 1 shows the UPLC chromatogram of extract I of *Silybum marianum* obtained according to Protocol 1.

I—Examples of Preparations of Extracts According to the Invention

Isopropanolic extract 90 (extract I) obtained by the following process:
  cold pressing of *Silybum marianum* achenes to obtain an oil from *Silybum marianum* achenes,
  extraction of the oil from *Silybum marianum* achenes by an isopropanol/water mixture (90/10 v/v) with 1 gram of the isopropanol/water mixture per gram of oil for 2 hours at 20° C.,
  recovery of the isopropanolic phase, and
  evaporation of the solvent.

Methanolic (extract M) and ethanolic 90 (extract E) extracts were obtained in a similar manner by replacing the isopropanol/water mixture (90/10 v/v) with methanol and an ethanol/water mixture (90/10 v/v) respectively. The extraction of the oil from *Silybum marianum* achenes is carried out with 3 volumes of methanol and 3 volumes of the ethanol/water mixture (90/10 v/v) for 1 volume of oil for 2 hours at 20° C., respectively.

These different extracts were characterized by ultra high-performance liquid chromatography (UPLC) or gas chromatography coupled with mass spectrometry (GC-MS) according to the protocols detailed below.

Protocols for Evaluating the Extracts Obtained:

1. Protocol 1: Evaluation of silymarin content by UPLC
   Preparation of sample and control:
   Silymarin control: Prepare a 5 mg solution of silymarin in 10 mL of methanol/water mixture (60:40) (v/v).
   Sample:
     Extract A: Prepare a solution of 100 mg of extract to be analyzed in 10 mL of a methanol/dichloromethane mixture (70:30) (v/v)
     Extracts M, E, I: Heat the dry extract to be analyzed to 35° C. with stirring until a homogeneous and clear solution is obtained. Weigh exactly 200 mg (pe) of the extract, solubilize it in 10 mL of a methanol/dichloromethane mixture allowing total solubilization of the extract and homogenize the solution. This mixture ranges from a methanol/dichloromethane ratio (1:1) (v/v) to pure methanol.
   Analytical conditions:
   Column: Acquity BEH Shield C18 150 mm×2.1 mm-1.7 µm (Waters)
   Mobile phase:
     A: Water+0.1% formic acid
     B: Acetonitrile+0.1% formic acid
   Gradient:

| T (min) | A (%) | B (%) |
| --- | --- | --- |
| 0 | 90 | 10 |
| 15 | 60 | 40 |
| 20 | 0 | 100 |

-continued

| T (min) | A (%) | B (%) |
|---|---|---|
| 39.5 | 0 | 100 |
| 40 | 90 | 10 |
| 45 | 90 | 10 |

Column temperature: 40° C.
Flow rate: 0.4 mL/min
Detection: 287 nm
Injection volume: 1 µL
2. Protocol 2: Evaluation of linoleic acid content by UPLC
Preparation of sample and control
Linoleic acid control: Prepare a solution of 10 mg linoleic acid in 10 mL of a 1:1 (v/v) methanol/dichloromethane mixture.
Sample:
Extracts M, E, I: Heat the dry extract to be analyzed to 35° C. with stirring until a homogeneous and clear solution is obtained. Weigh exactly 50 mg (pe) of the extract, solubilize it in 1 mL of a methanol/dichloromethane mixture allowing total solubilization of the extract and homogenize the solution. This mixture ranges from a methanol/dichloromethane ratio (1:1) (v/v) to pure methanol.
Analytical conditions
Column: Acquity BEH Shield C18 150 mm×2.1 mm-1.7 µm (Waters)
Mobile phase:
A: Water+0.1% formic acid
B: Acetonitrile+0.1% formic acid
Gradient:

| T (min) | A (%) | B (%) |
|---|---|---|
| 0 | 50 | 50 |
| 1 | 50 | 50 |
| 10 | 0 | 100 |
| 15 | 0 | 100 |
| 15.5 | 50 | 50 |
| 20 | 50 | 50 |

Column temperature: 40° C.
Flow rate: 0.4 mL/min
Detection: 215 nm
Injection volume: 1 µL
3. Protocol 3: Evaluation of fatty acid and sterol content by GC-MS
Sample preparation
Heat the dry extract to be analyzed to 35° C. while stirring until a clear homogeneous liquid is obtained.
Solubilize 20 mg of the extract in 800 µL of methanol/dichloromethane (1:1) (v/v) mixture
Add 200 µL of the derivatization reagent N,O-Bis(trimethylsilyl)trifluoroacetamide (BSTFA)+Trimethylchlorosilane (TMCS) (99:1) (Supelco—Sigma Aldrich)
Vortex for 1 minute
Gas chromatography (GC) conditions
Column: DB-5 ms (Agilent technologies); 30 m×0.25 mm; 0.25 µm
Injection: T=300° C.; Mode=Split; Split ratio=100:1
Oven: Temperature gradient (° C.):
Initial temperature=150° C.
Gradient=7° C./min up to final temperature=340° C.
Maintain at 340° C. for 10 minutes
Carrier gas flow rate: 1 mL/min
Detection: MS-EI; T=300° C.; Scan Time=0.2 sec; Full Scan Start Mass=40; Full Scan End Mass=600
Injection volume: 1 µL
Results:
Extract I contain mostly substances with a retention time between 13 and 30 minutes per UPLC (see FIG. 1). It has the following characteristics:

| Components | % by weight |
|---|---|
| Silymarin | 0.06 |
| Free fatty acids (mainly palmitic, oleic and linoleic acids) | 24.6 |
| of which linoleic acid | 5.1 |
| Sterols | 3.6 |
| of which beta-sisterol | 1.5 |

Figure 2:
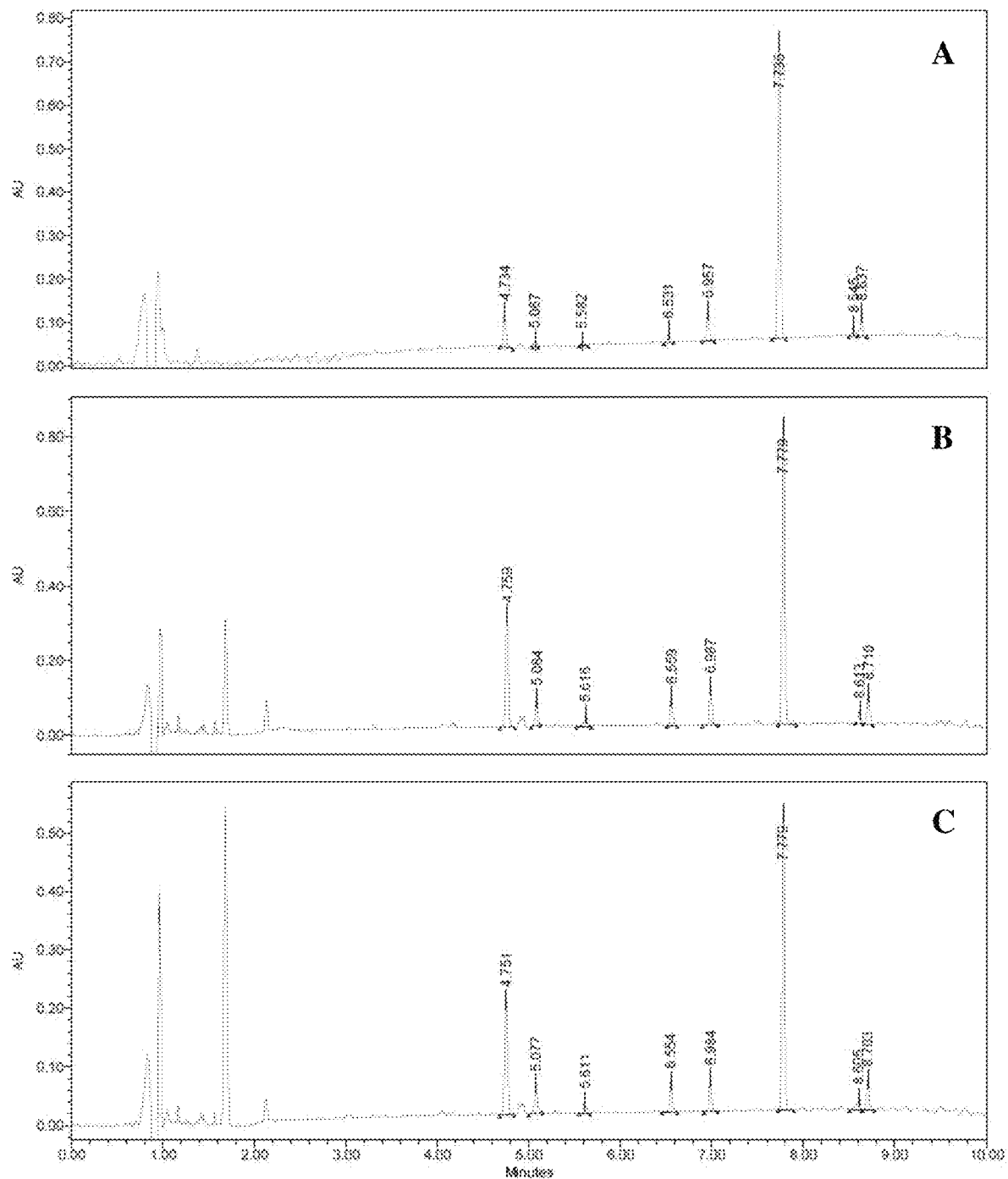
FIGS. 2A, 2B and 2C represent respectively a UPLC chromatogram of extract M, extract E and extract I of *Silybum marianum* obtained according to Protocol 2.
Figure 3:
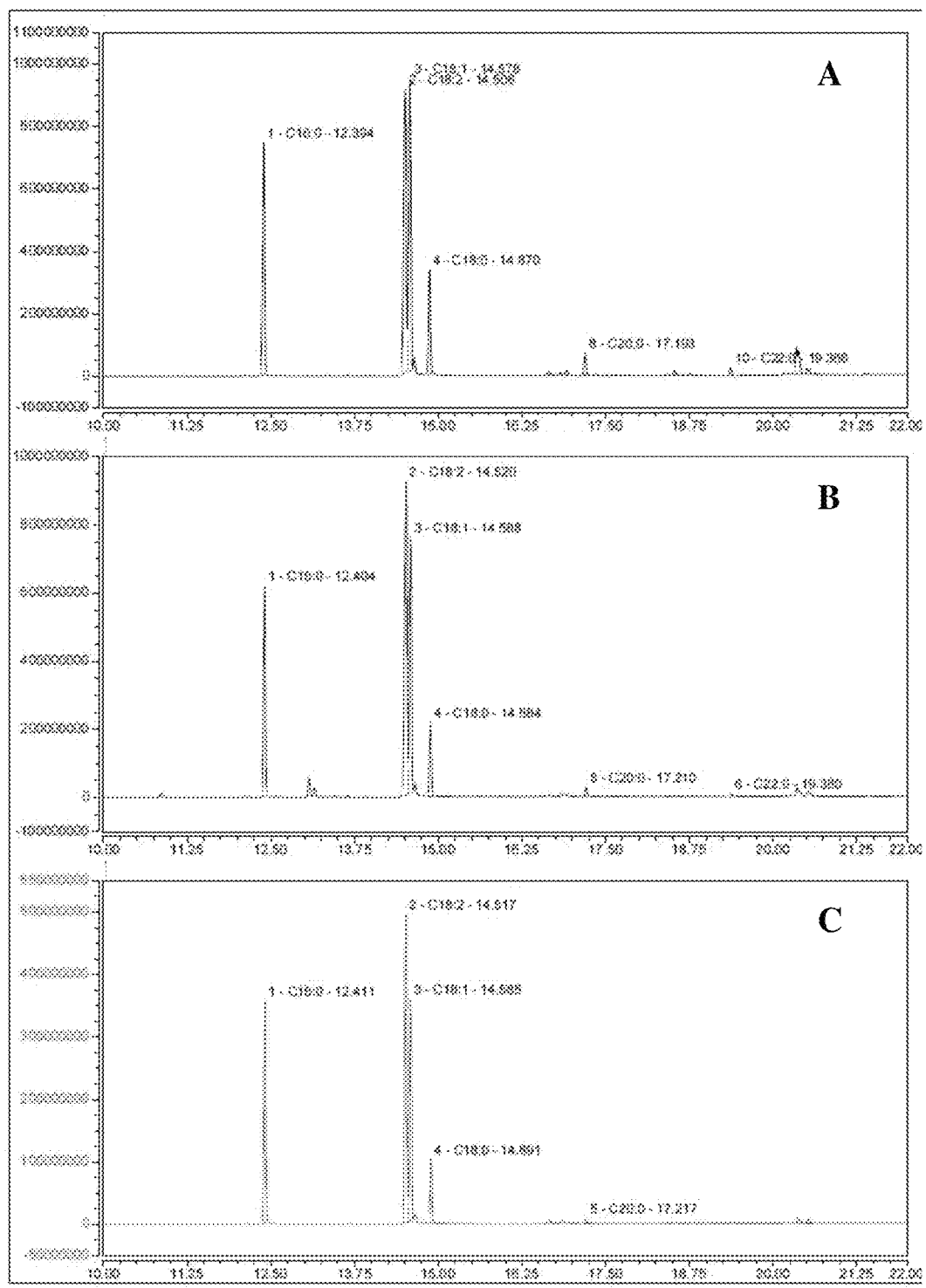
FIGS. 3A, 3B and 3C represent respectively the 10-22 min zone (corresponding to the fatty acid zone) of a GC/MS chromatogram of extract E, extract M and extract I of *Silybum marianum* obtained according to Protocol 3.
Figure 4:
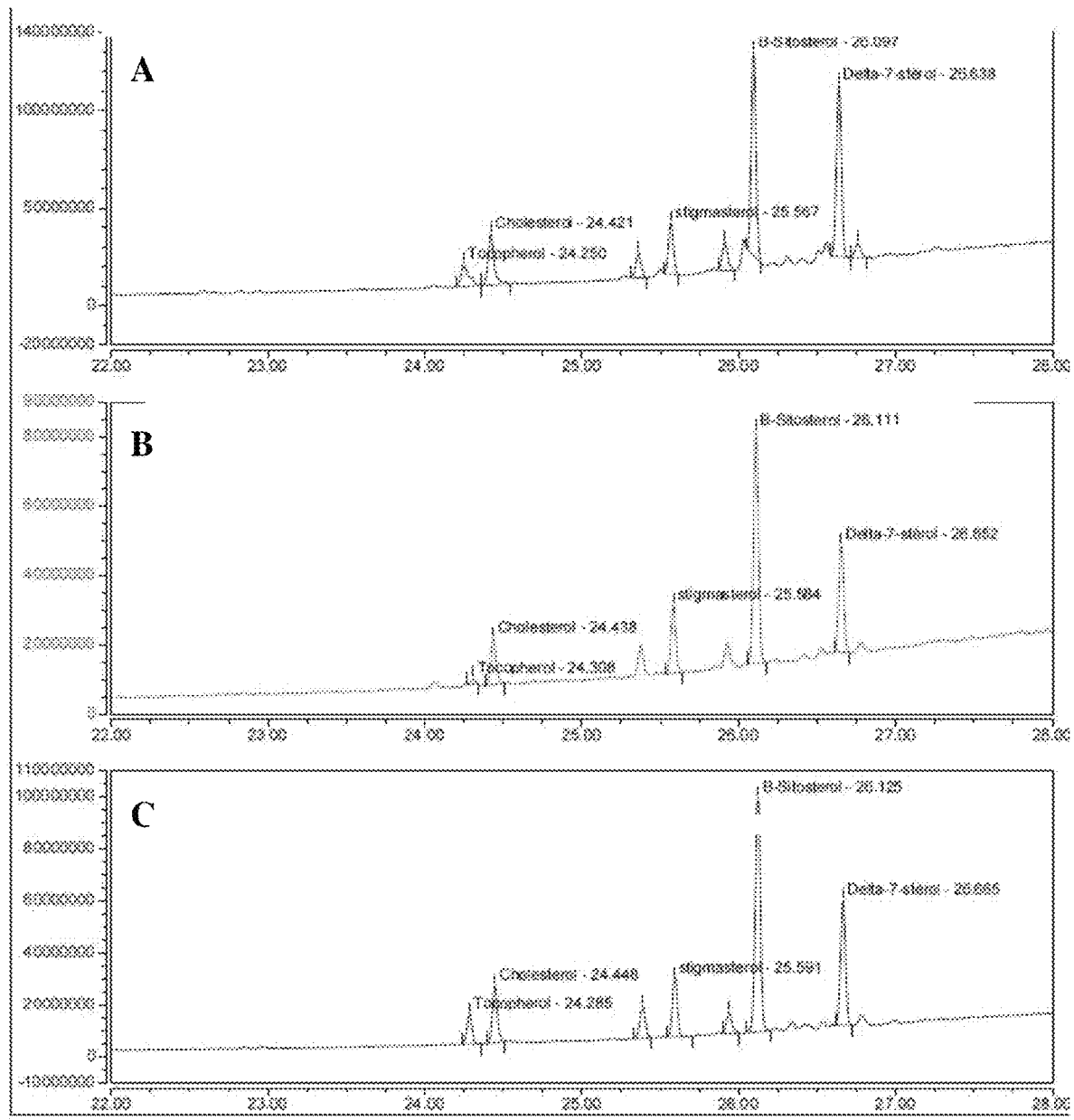
FIGS. 4A, 4B and 4C represent respectively the 22-28 min zone (corresponding to the sterol zone) of a GC/MS chromatogram of extract E, extract M and extract I of *Silybum marianum* obtained according to Protocol 3.

The UPLC and GC/MS chromatograms of the 3 extracts (extracts I, M and E) of Silybum marianum are similar (see FIGS. 2 and 3).

II—Examples of Compositions Comprising a Retinoid and/or an Extract of Silybum marianum According to the Invention Composition 1 (Cream) Based on Retinaldehyde=RAL1

| INCI designation | Percentage by weight |
|---|---|
| Glycylglycine oleamide | 0.1% |
| Tocopheryl glucoside | 0.1% |
| Retinaldehyde | 0.05% |
| Gelling carbomer | 0.35% |
| Squalane | 15% |
| Mineral oil | |
| Caprylic capric triglycerides | |
| Water | q.s. 100% |

Composition 2 (Cream) Based on Retinaldehyde=RAL2

| INCI designation | Percentage by weight |
|---|---|
| Water | 100% Q.S. |
| Potassium sorbate | 0.3 |
| Ethanol | 3 |
| Glycolic acid | 6 |
| Ceteareth 33 & cetearyl alcohol | 3 |
| Polysorbate 60 | 6 |
| Cetyl alcohol | 11 |
| Butylhydroxytoluene | 0.01 |
| Cyclopentasiloxane | 10 |
| Sodium hydroxide | q.s. |
| Retinaldehyde | 0.1 |
| Undecyl rhamnoside | 0.2 |

Composition 3 (Cream) Based on Retinaldehyde=RAL3

| INCI designation | Percentage by weight |
|---|---|
| Water | 100% Q.S. |
| Glycerin | 6 |
| Disodium EDTA | 0.1 |
| Pentylene glycol | 3 |
| Glyceryl Stearate & PEG-100 Stearate | 3 |
| Isododecane | 7 |
| Butylhydroxytoluene | 0.02 |
| Carbomer papain crosspolymer | 1 |
| Retinaldehyde | 0.1 |
| Caprylic/capric triglycerides | 7 |
| 2-Hydroxy-octyl 1α-linolenate | 0.6 |

Composition 4 (Cream) Based on Retinaldehyde=RAL4

Retinaldehyde was formulated at 0.1% (w/w) in a mixture comprising:
5% glycerin
1.5% gelling agent
1% silica
q.s. water.

Composition 5 (Cream) Based on *Silybum marianium* Extract=SYL1

Extract I prepared in Example 1 was formulated at 7% (w/w) in a mixture of isopropanol/PEG 300 (1:1) (w/w).

Composition 6 (Cream) Based on *Silybum marianium* Extract=SYL2 (Percentage w/w)
25% SYL1
5% glycerin
1.5% gelling agent
1% silica
q.s. water.

Composition 7 (Cream) Comprising the Combination of an Extract of *Silybum marianum* and Retinaldehyde=ASSO1 (Percentage w/w)
25% SYL1
0.1% retinaldehyde
5% glycerin
1.5% gelling agent
1% silica
q.s. water.

Composition 8 (Cream) Comprising the Combination of an Extract of *Silybum marianum* and Retinaldehyde=ASSO2 (Percentage w/w)
12.5% SYL1
0.1% retinaldehyde
5% glycerin
1.5% gelling agent
1% silica
q.s. water.

III—Clinical Studies

The different creams tested were applied to the face (cleansed skin), 2 applications/day morning and evening by gentle massage except for compositions containing RAL: in the evening only.

The analysis of the therapeutic effects obtained was carried out according to the Investigator Global Assessment (IGA) method accepted by the Food and Drug Administration (FDA)—for acne and suitable for rosacea and seborrheic dermatitis—and applied by a clinical dermatologist (Guidance for Industry Acne Vulgaris: Developing Drugs for Treatment).

With such a method, the following IGA Grades are assigned according to the severity of the acne observed:

| Grade IGA | Patient's condition |
|---|---|
| 0 | Clear skin without inflammatory or non-inflammatory lesions |
| 1 | Nearly clear skin with rare non-inflammatory lesions and not more than one small inflammatory lesion |
| 2 | Mild acne of severity greater than grade 1: some non-inflammatory lesions with no more than a few inflammatory lesions (papules and pustules, no nodular lesions) |
| 3 | Moderate acne of severity greater than grade 2: up to many non-inflammatory lesions and potentially some inflammatory lesions but no more than one small nodular lesion. |
| 4 | Severe acne of severity greater than grade 3: up to numerous non-inflammatory and inflammatory lesions but no more than a few nodular lesions |

The results of the various analyses are presented below.

Analysis 1: Before Treatment Versus *Silybum marianum* Extract without RAL Versus Combination RAL+*Silybum marianum* Extract

| Patients | Protocol (number of successive weeks of the same treatment and second treatment applied on the day following the end of the 1st treatment) | Before treatment | After treatment *Silybum marianum* extract | After treatment RAL + *Silybum marianum* extract |
|---|---|---|---|---|
| Man with rosacea and seborrheic dermatitis | 35 weeks SYL1 then 15 weeks SYL1 + RAL1 | 2 | 1 | 0 |
| Woman with rosacea and seborrheic dermatitis | 9 weeks SYL1 then 50 weeks SYL1 + RAL1 | 4 | 2 | 0 |
| Man with rosacea and seborrheic dermatitis | 3 weeks SYL1 then 18 weeks SYL1 + RAL1 | 3 | 1 | 0 |
| Woman with late acne | 5 weeks SYL1 then 8 weeks SYL1 + RAL2 | 3 | 2 | 1 |
| Teenager (male) with acne | 5 weeks SYL1 then 5 weeks SYL1 + RAL3 | 3 | 1 | 0 |
| Teenager (female) with acne | 4 weeks SYL1 then 28 weeks SYL1 + RAL3 | 2 | 1 | 0 |
| Teenager (male) with acne | 52 weeks SYL1 then 16 weeks SYL1 + RAL3 | 3 | 1 | 0 |
| Woman with late acne | 10 weeks SYL1 then 20 weeks SYL1 + RAL3 | 3 | 2 | 1 |

|  | Protocol (number of successive weeks of the same treatment and second treatment applied on the day following the end of the 1st treatment) | IGA Grade | | |
|---|---|---|---|---|
| Patients | | Before treatment | After treatment Silybum marianum extract | After treatment RAL + Silybum marianum extract |
| Woman with late acne | 8 weeks SYL1 then 8 weeks SYL1 + RAL3 | 3 | 2 | 2 |
| Woman with late acne | 24 weeks SYL2 then 4 weeks ASSO1 | 3 | 2 | 1 |
| Teenager (female) with acne | 4 weeks SYL2 then 6 weeks ASSO1 | 2 | 1 | 0 |
| Teenager (male) with acne | 16 weeks SYL2 then 3 weeks ASSO1 | 3 | 2 | 1 |
| Woman with late acne | 6 weeks SYL2 then 3 weeks ASSO1 | 3 | 2 | 1 |
| Woman with late acne | 8 weeks SYL2 then 8 weeks ASSO2 | 3 | 2 | 1 |
| Teenager (female) with acne | 12 weeks SYL1 then 10 weeks ASSO2 | 4 | 2 | 1 |

Analysis 2: Before Treatment Versus RAL without *Silybum marianum* Extract Versus Combination RAL+*Silybum marianum* Extract

|  | Protocol (number of successive weeks of the same treatment and second treatment applied on the day following the end of the first treatment) | IGA Grade | | |
|---|---|---|---|---|
| Patients | | Before treatment | After treatment RAL | After treatment RAL + Silybum marianum extract |
| Man with seborrheic dermatitis + bald scalp | 35 weeks RAL1 then 43 weeks SYL1 + RAL1 | 3 | 2 | 1 |
| Woman with late acne | 6 weeks RAL 3 then 6 weeks SYL1 + RAL3 | 4 | 3 | 1 |
| Woman with late acne | 8 weeks RAL2 Then 8 weeks SYL1 + RAL2 | 3 | 2 | 1 |
| Teenager (female) with acne | 60 weeks RAL2 Then 16 weeks SYL1 + RAL2 | 3 | 2 | 1 |
| Teenager (male) with acne | 6 weeks RAL3 then 20 weeks SYL1 + RAL3 | 3 | 2 | 1 |
| Woman with late acne | 8 weeks RAL3 Then 4 weeks ASSO1 | 4 | 3 | 2 |

Conclusion

The results obtained with the different treatments based respectively on a combination of retinaldehyde and *Silybum marianum* extract, retinaldehyde alone or *Silybum marianum* extract alone, in the clinical studies described above, show that retinaldehyde in combination with *Silybum marianum* extract, allows a better clinical result to be obtained.

IV—In Vitro Studies: Evaluation of the Correction of Vitamin A Deficiency by the Combination Retinaldehyde (RAL) or Retinol (ROL)+*Silybum marianum* Extract (SYL)

Materials and Methods:

Culture:
3 days prior to the experiment, culture A431 epidermoid carcinoma cells in 2 6-well plates at a density of 40,000 cells per well (2 mL per well).

Cell treatment (3 wells per condition, 2 mL per well; final concentrations):
Ethanol (solvent): 1% ethanol:
ROL: 10 µM ROL in 1% ethanol:
RAL: 2 µM RAL in 1% ethanol:
SYL: 50 µg/mL Extract I of *Silybum marianum* in 1% ethanol:
ROL+SYL: 10 µM ROL+50 µg/mL *Silybum marianum* extract in 1% ethanol;
RAL+SYL: 2 µM RAL+50 µg/mL *Silybum marianum* extract in 1% ethanol.
Incubation: 1 h Cell Harvest:
Remove the medium, wash twice with PBS (phosphate saline buffer);
Add 500 µL per well of EDTA-NaOH (0.02% ethylene diamine tetraacetic acid (EDTA)+200 µM NaOH), allow to stand for 10-15 minutes, then detach the cells with a rubber scraper and transfer to extraction glass tubes;
Add 10 µL of 20 mM HCl, sonicate briefly, then transfer 10 µL of suspension to 1.5 mL Eppendorf tubes for protein determination;
To the glass tubes add 500 µL of 200 µM butylated hydroxytoluene (BHT)/ethanol, 20 µL of 20 µM retinyl acetate (internal standard), then 4 mL of hexane;
Vortex vigorously for 30 sec, then centrifuge the tubes (900 g, 5 min);
Transfer the supernatant into uncapped glass tubes, evaporate dry under nitrogen;
Reconstitute in 200 µL of methanol, then transfer to high-performance liquid chromatography (HPLC) vials.

Retinoid Analysis by HPLC:
Agilent 1100 HPLC chain with quaternary pump and DAD detector Macherey-Nagel column Nucleodur C18 pyramid 3 µm
mobile phase:
  0-6 min: 100% methanol
  6-8 min: linear gradient to methanol/THF (4:1)
  8-18 min: methanol/THF (4:1)
  18-20 min: linear gradient to 100% methanol
  20-30 min: 100% methanol
detection: 325 nm (retinol, retinyl esters); 383 nm (retinal).

Figure 5:
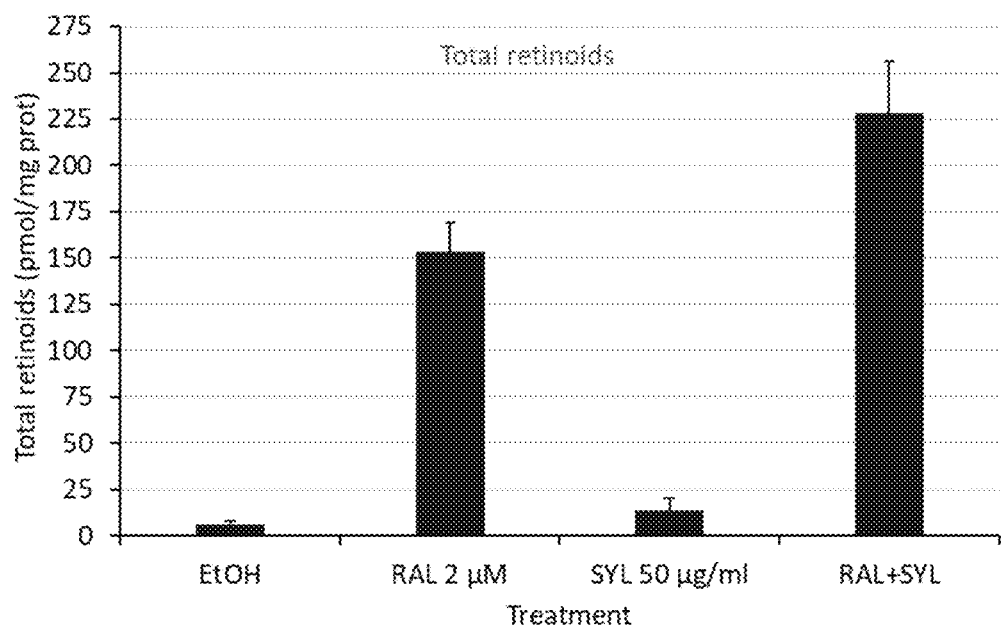
FIG. 5 represents the amount produced by skin cells of total retinoids as a function of the treatment received, i.e. vehicle (EtOH) alone, 2 µM retinaldehyde (2 µM RAL), 50 µg/mL *Silybum marianum* extract (50 µg/mL SYL) or the combination of 2 µM retinaldehyde and 50 µg/mL *Silybum marianum* extract (RAL+SYL).
Figure 6:
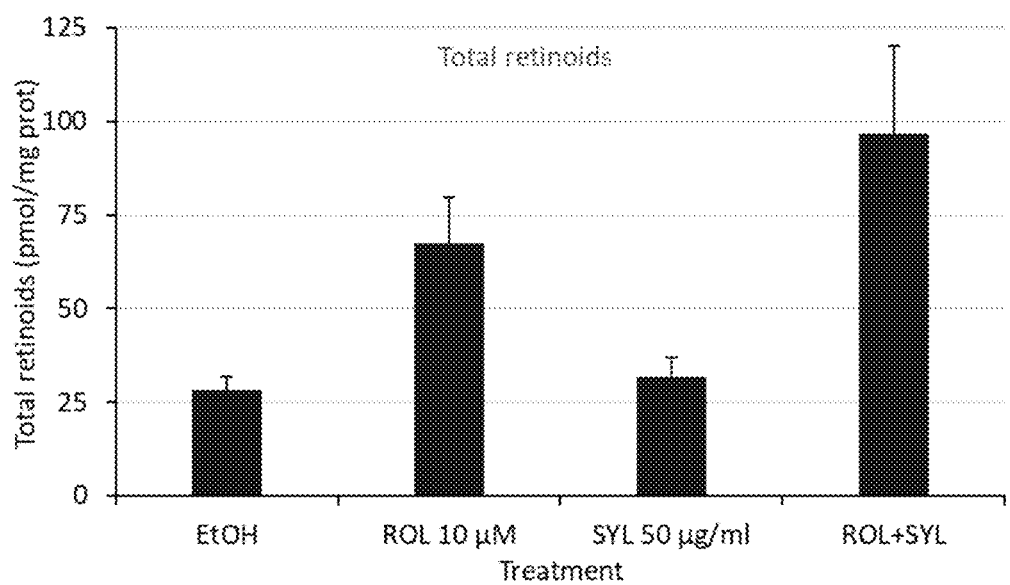
FIG. 6 represents the amount produced by skin cells of total retinoids as a function of the treatment received, i.e. vehicle (EtOH) alone, 2 µM retinol (2 µM ROL), 50 µg/mL *Silybum marianum* extract (50 µg/mL SYL) or the combination of 2 µM retinol and 50 µg/mL *Silybum marianum* extract (ROL+SYL).

Results:

The results obtained are presented in FIGS. 5 and 6.

Conclusion:

*Silybum marianum* extract alone does not induce significant retinoid production.

On the other hand, skin cells produce significantly more retinoids in the presence of the combination of an extract of *Silybum marianum* with retinaldehyde or retinol than in the presence of retinaldehyde or retinol alone, demonstrating the synergistic effect of the combination according to the invention.

The invention claimed is:

1. An active ingredient combination consisting of a retinoid and an extract of *Silybum marianum* (L.) Gaertn.,
   wherein the retinoid is retinaldehyde, and
   wherein the extract of *Silybum marianum* (L.) Gaertn. is an extract of achenes of *Silybum marianum* (L.) Gaertn. comprising less than 0.2% by weight of silymarin based on the weight of the dry extract.

2. The combination according to claim 1, wherein the extract of *Silybum marianum* (L.) Gaertn. is an achene extract of *Silybum marianum* (L.) Gaertn. comprising less than 0.1% by weight of silymarin based on the weight of the dry extract.

3. The combination according to claim 1, wherein the extract of *Silybum marianum* (L.) Gaertn. contains between 0.5% and 2.5% by weight of beta-sitosterol based on the weight of the dry extract.

4. The combination according to claim 1, wherein the extract of *Silybum marianum* (L.) Gaertn. contains between 1.0% and 2.0% by weight of beta-sitosterol based on the weight of the dry extract.

5. The combination according to claim 1, wherein the extract of *Silybum marianum* (L.) Gaertn. contains between 2 and 7% by weight of sterols based on the weight of the dry extract.

6. The combination according to claim 1, wherein the extract of *Silybum marianum* (L.) Gaertn. contains between 3 and 5% by weight of sterols based on the weight of the dry extract.

7. The combination according to claim 1, wherein the extract of *Silybum marianum* (L.) Gaertn. contains between 3% and 15% by weight of free linoleic acid based on the weight of the dry extract.

8. The combination according to claim 1, wherein the extract of *Silybum marianum* (L.) Gaertn. contains between 4% and 10% by weight of free linoleic acid based on the weight of the dry extract.

9. The combination according to claim 1, wherein the extract of *Silybum marianum* (L.) Gaertn. contains between 10% and 50% by weight of free fatty acids based on the weight of the dry extract.

10. The combination according to claim 1, wherein the extract of *Silybum marianum* (L.) Gaertn. contains between 10% and 30% by weight of free fatty acids based on the weight of the dry extract.

11. The combination according to claim 1, wherein the extract of *Silybum marianum* (L.) Gaertn. comprises between 0.01% and 0.5% by weight of tocopherols based on the weight of the dry extract.

12. A method for treating acne, seborrhea, rosacea or seborrheic dermatitis comprising administering to a person in need thereof an effective amount of a combination according to claim 1.

13. A dermatological or dermocosmetic composition comprising the active ingredient combination according to claim 1 and at least one dermatologically or dermocosmetically acceptable excipient, wherein the sole active ingredient of the composition consists of the active ingredient combination.

14. The dermatological or dermocosmetic composition according to claim 13, comprising 0.01 to 10% by weight of the extract of *Silybum marianum* (L.) Gaertn. by weight of dry extract based on the total weight of the composition.

15. The dermatological or dermocosmetic composition according to claim 13, comprising 0.001 to 5% by weight of the retinoid based on the total weight of the composition.

16. The dermatological or dermocosmetic composition according to claim 13, being intended for topical application.

17. A method for treating acne, seborrhea, rosacea or seborrheic dermatitis comprising administering to a person in need thereof an effective amount of a dermatological or dermocosmetic composition according to claim 13.

* * * * *